(12) United States Patent
Hoenes

(10) Patent No.: US 8,574,169 B2
(45) Date of Patent: Nov. 5, 2013

(54) TEST DEVICE IN PARTICULAR FOR BLOOD SUGAR TESTS

(75) Inventor: Joachim Hoenes, Zwingenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/235,027

(22) Filed: Sep. 16, 2011

(65) Prior Publication Data

US 2012/0071791 A1 Mar. 22, 2012

Related U.S. Application Data

(63) Continuation of application No. PCT/EP2010/053298, filed on Mar. 15, 2010.

(30) Foreign Application Priority Data

Mar. 17, 2009 (EP) .................................... 09155318

(51) Int. Cl.
*A61B 5/151* (2006.01)
*A61B 5/157* (2006.01)

(52) U.S. Cl.
USPC ........... 600/583; 600/573; 606/181; 606/182; 606/183; 606/184; 606/185; 606/186

(58) Field of Classification Search
USPC ............................. 600/573, 583; 606/181–186
See application file for complete search history.

(56) References Cited

U.S. PATENT DOCUMENTS

| | | | |
|---|---|---|---|
| 7,396,334 B2* | 7/2008 | Kuhr et al. | 600/583 |
| 7,479,119 B2* | 1/2009 | Roe | 600/584 |
| 7,815,579 B2* | 10/2010 | Roe | 600/584 |
| 7,935,063 B2* | 5/2011 | Roe | 600/584 |
| 8,043,317 B2* | 10/2011 | Fritz et al. | 606/181 |
| 8,052,926 B2* | 11/2011 | Joseph et al. | 422/22 |
| 8,323,212 B2* | 12/2012 | Sakata | 600/573 |
| 2003/0050573 A1* | 3/2003 | Kuhr et al. | 600/567 |
| 2003/0153939 A1 | 8/2003 | Fritz et al. | |
| 2004/0260325 A1* | 12/2004 | Kuhr et al. | 606/181 |
| 2005/0177072 A1* | 8/2005 | Kloepfer et al. | 600/583 |
| 2006/0174592 A1* | 8/2006 | Chan | 53/442 |
| 2006/0200045 A1* | 9/2006 | Roe | 600/583 |
| 2006/0293611 A1* | 12/2006 | Calasso et al. | 600/583 |
| 2007/0167869 A1* | 7/2007 | Roe | 600/583 |
| 2008/0103415 A1* | 5/2008 | Roe et al. | 600/583 |
| 2008/0243032 A1* | 10/2008 | Hindelang et al. | 600/583 |
| 2008/0249435 A1* | 10/2008 | Haar et al. | 600/583 |
| 2009/0043325 A1 | 2/2009 | Fritz et al. | |
| 2011/0034829 A9* | 2/2011 | Freeman | 600/583 |

FOREIGN PATENT DOCUMENTS

| | | |
|---|---|---|
| WO | 2004086970 A1 | 10/2004 |
| WO | 2006082106 A1 | 8/2006 |
| WO | 2008043565 A2 | 4/2008 |

* cited by examiner

*Primary Examiner* — Sean Dougherty
(74) *Attorney, Agent, or Firm* — Harness, Dickey

(57) ABSTRACT

The invention concerns a test device, in particular for blood sugar tests, comprising a lancing element which is provided with a lancing component for producing a skin puncture, and a protecting element shielding the lancing element at least in the area of the lancing component. According to the invention it is proposed that the lancing element has a collecting structure for collecting body fluid from the skin puncture and that the protecting element comprises a protecting foil to cover the collecting structure and a holding body for holding the protecting foil on the lancing element.

15 Claims, 2 Drawing Sheets

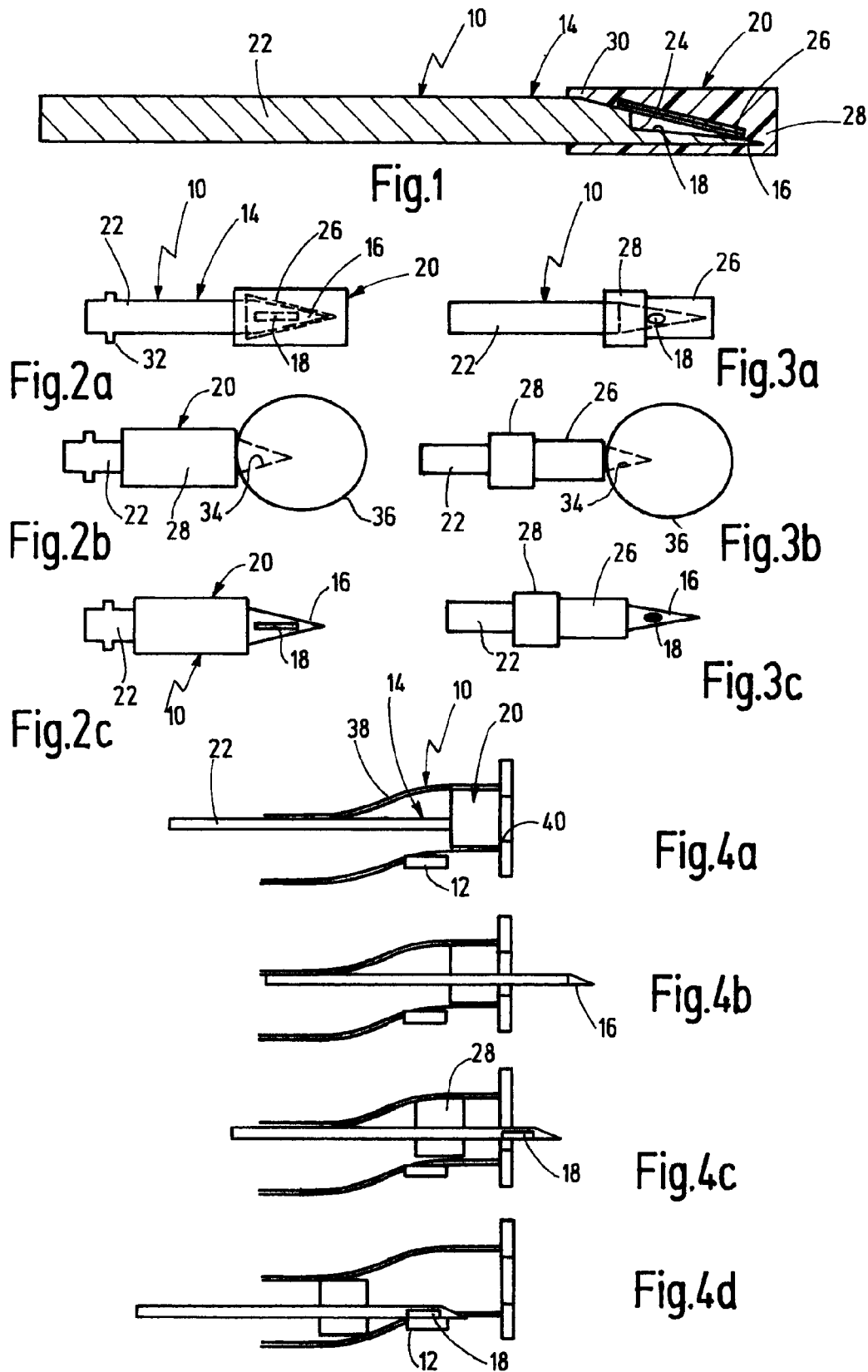

TEST DEVICE IN PARTICULAR FOR BLOOD SUGAR TESTS

CROSS-REFERENCE TO RELATED APPLICATIONS

Figure 5A:
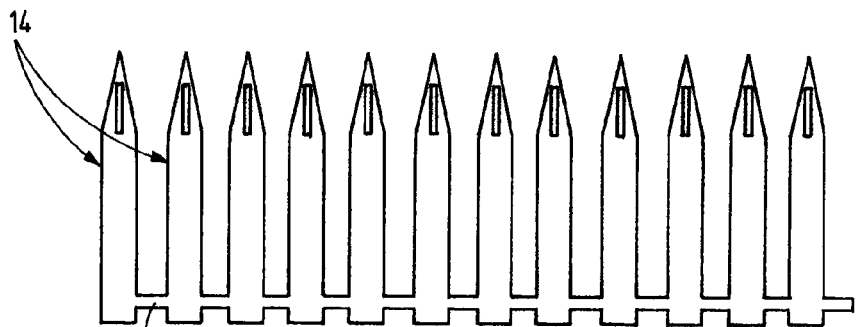
Figure 5B:
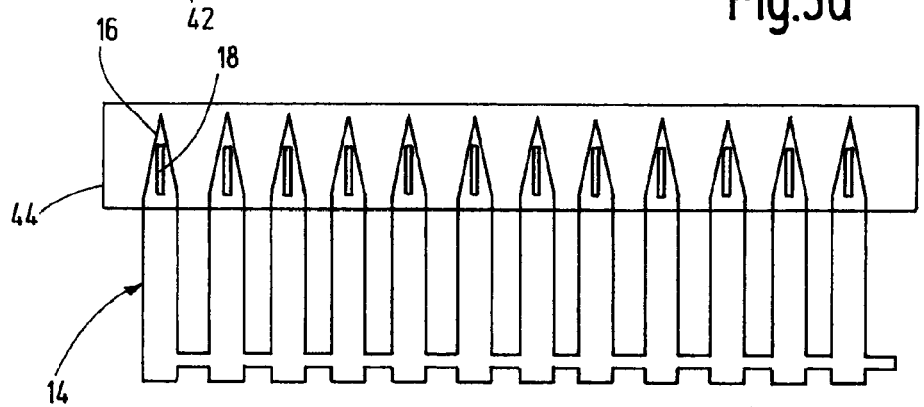
Figure 5C:
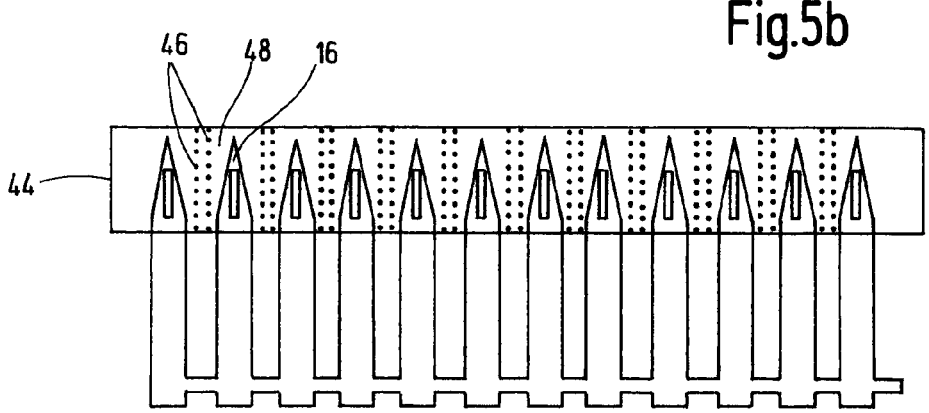

This application is a continuation of International Application No. PCT/EP2010/053298, filed Mar. 15, 2010, which claims the benefit and priority of European Patent Application No. 09155318.0, filed Mar. 17, 2009. The entire disclosures of the above applications are incorporated herein by reference.

BACKGROUND

The invention concerns a test device, in particular for blood sugar tests, comprising a lancing element which is provided with a lancing component for producing a skin puncture, and a protecting element shielding the lancing element at least in the area of the lancing component. The invention additionally concerns a production process for such a test device.

Needles or lancets for obtaining body fluids for blood sugar tests must be sterile before they are inserted into the skin. For this purpose the needle tips are usually packaged germ-tight and, for example, sterilized by irradiation. The packaging keeps the tips sterile until they are removed. For manual use it is usual to twist off or pull off a plastic part surrounding the tip. It is known from International Publication No. WO 01/66010, Fritz et al., published Sep. 13, 2001 (see also U.S. Patent Application Publication No. 2003/0153939, Fritz et al., published Aug. 14, 2003) in connection with automated lancing devices that an elastomer part embedding the tip can be pierced directly during the lancing process.

SUMMARY

Based on this, an object of the invention is to further improve the products and production processes known in the prior art and to design them such that a hygienic and simple handling is ensured in the production, storage and use of such disposable test devices. In particular, the present invention provides test devices, such as for blood sugar tests, comprising a lancing element which is provided with a lancing component for producing a skin puncture, and a protecting element shielding the lancing element at least in the region of the lancing component, characterized in that the lancing element has a collecting structure for collecting body fluid from the skin puncture and that the protecting element comprises a protecting foil to cover the collecting structure and a holding body formed onto the lancing element for holding the protecting foil.

The invention is based on the idea of using a composite structure as a protecting element for a system with an integrated sample collecting structure so that the specific advantages of the composite partners complement one another. Accordingly it is proposed according to the invention that the lancing element has a collecting structure for collecting body fluid from the skin puncture and that the protecting element comprises a protecting foil to cover the collecting structure and a holding body that is attached to the lancing element and preferably moulded-on by means of a moulding tool and in particular injection-moulded for holding the protecting foil. The collecting structure enables sample collection already during the puncture required to access the sample so that the handling is simplified for the user. The protecting foil prevents moulded material of the protecting element from unintentionally penetrating into the collecting structure from which it is hardly possible to completely remove it during the lancing process. The rigid or solid holding body provides the necessary structural rigidity and allows the foil to be held also in the production process and ensures a tight connection to the lancing element. The protecting foil is preferably completely embedded in the holding body. In this connection it must be borne in mind that a foil packaging alone must surround the complete lancing element in order to ensure the necessary sterility. However, considerable effort would be required to completely and in every individual case reliably remove such a packaging from the collecting structure such that sample collection and optionally sample transfer can take place unhindered.

The collecting structure is advantageously formed by a recess in the lancing component that can be filled with body fluid and is in particular in the form of a groove that is open on one side or a cut-out that is open on both sides in order to simplify the production and also to be able to collect very small amounts of sample, wherein the recess is completely covered by the protecting foil when the lancing element is in the unused state and thus the surface properties in the storage state are hardly impaired.

It is advantageous for the collection of aqueous samples when the lancing element has a hydrophilic coating which is covered by the protecting foil at least in some areas and thus remains stable in storage.

In order to abolish the protecting function when in use, the protecting foil and the holding body can be in a common movable arrangement on the lancing element or capable of being jointly removed therefrom so that the lancing component and the collecting structure are exposed when the lancing element is in use.

In this connection it is particularly advantageous when the lancing component can be inserted into the skin while piercing the holding body and/or the protecting foil.

Another improvement in this connection provides that the protecting element forms a stop against the skin or against an abutment when the skin puncture is produced.

In order to simply adapt it to the specific collecting structure, the protecting foil can form a two-layered foil envelope or a single-layered foil cover.

Due to the attachment to the holding structure it is sufficient when the protecting foil rests loosely on the lancing component or is releasably adhesively connected therewith so that unwanted displacement in the production process is also avoided.

A further advantageous embodiment provides that the solid holding body forms a permanent composite with the protecting foil wherein the holding body completely encloses the protecting foil or encloses the protecting foil at one end section. Such a permanent connection can be simply created in an injection moulding process as a result of heating the material.

Furthermore, it is advantageous when the holding body is designed as an injection-moulded part preferably made of an elastomer material and is directly injection-moulded onto the lancing element. In a particularly preferred embodiment the holding body encases a shaft of the lancing element.

In order to achieve a reliable attachment and sterile screening, it is advantageous when the holding body is connected to the lancing element preferably in the area of an edge part reaching over the protecting foil in a germ-tight or sterile-tight manner so that germs cannot penetrate up to the lancing component until directly before use. Hence, the protecting element maintains the sterility of the lancing component in the unused state and/or enables at least the lancing component to be hygienically disposed of in the used state. Such a germ-tight connection is created by a directly adhering material connection so that no crevices, gaps, holes or other leakages in the range of more than 10 micrometers passage width occur in the sealing area.

A further increase in the system integration with a simplified handling potential results from the fact that the collecting structure to which body fluid is applied can be brought into contact with an analytical test element that reacts to an analyte in the body fluid by means of a transfer movement so that body fluid is transferred directly from the collecting structure onto the test element without requiring a larger flow path. In this connection it is also of particular advantage when the holding body forms a guiding member to control the movement of the lancing element.

With regard to the process, the object mentioned above is achieved in that a lancing element is covered with a protecting foil at least in the area of a collecting structure and that a holding body for the protecting foil is directly moulded onto the lancing element. The lancing element is preferably encased on a shaft. Such a structure can then, for example, be permanently sterilized by irradiation. For mass production it is advantageous when a plurality of lancing elements in a tape-shaped or ring-shaped arrangement are covered with a protecting foil at least in the area of a respective collecting structure and subsequently a holding body for the protecting foil is moulded onto the lancing elements.

DRAWINGS

The invention is further elucidated in the following on the basis of the embodiment examples shown schematically in the drawing.

FIG. 1 shows a test device for blood sugar tests in the form of a microsampler with a protecting element in a longitudinal section;

FIGS. 2a-c and 3a-c each show a further embodiment of a microsampler with a protecting element in various states of use;

FIG. 4a-d shows an embodiment of a microsampler stored in combination with a test element in various stages of sample collection; and FIG. 5a-d shows successive process steps in the production of microsamplers with a protecting element.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

The test devices 10 shown in the drawing can each be used in a hand-held device as microsamplers (microsample collectors) optionally in combination with a test element 12 in the form of a disposable part for collecting and analyzing a body fluid such as blood or tissue fluid. For this purpose they comprise a lancing element 14 which is provided with a distal lancing member or lancing component 16 for insertion into the skin and a collecting structure 18 for collecting body fluid, and a protecting element 20 for shielding the lancing element 14 at least in the area of the lancing member and the collecting structure.

The lancet-like lancing element 14 shown in FIG. 1 has a shaft 22 on the distal end of which a needle tip is configured as a lancing component 16. The collecting structure 18 is formed by an axial capillary groove that is open on one side, in the area of the needle tip. In order to improve liquid uptake, the metallic lancing element 14 is provided with a hydrophilic coating 24 at least in the distal area.

In the unused stand-by state of the device, the protecting element 20 is in an active position over the distal end section of the lancing element 14. The protecting element 20 consists of a flexible protecting foil 26 for covering at least the collecting structure 18 and of a dimensionally-stable or rigid holding body 28 for holding the protecting foil 26 on the lancing element 14. In the example shown in FIG. 1, the protecting foil 26 rests on one side over the collecting structure 18 as a loose or optionally lightly adhering one-layered foil cover. The holding body 28, solidly constructed as an injection-moulded part made of an elastomer material, completely encases the protecting foil 26 and an end section 30 thereof reaching proximally over the protecting foil 26 is connected tightly to the shaft 22 against the penetration of germs. In this manner the area of the lancing component 16 of the lancing element 14 can be kept ready while maintaining sterility and while mechanically shielded, whereas the protecting foil 26 borders at least the receiving volume of the collecting structure 18 in a material-tight manner and thus also maintains the hydrophilicity of the coating 24 over a long storage period.

The protecting element 20 is arranged on the lancing element 14 such that it can be displaced in the axial direction of the shaft 22, thus exposing the lancing component 16 and the collecting structure 18 in a state of use as will be further elucidated in the following. It is also conceivable that the protecting element 20 can be returned into its initial position after the lancing process in order to enable a hygienic and safe disposal of the lancing element 14.

The embodiment shown in FIG. 2 differs essentially only in that the protecting foil 26 encloses all sides of the needle tip 16 as a two-layered foil envelope or pouch and in that the collecting structure 18 is formed by a continuous slot at right angles to the longitudinal axis of the shaft 22 which is therefore covered on both side openings by the protecting foil 26 in the stand-by state shown in FIG. 2a. A radially projecting coupling part 32 on the shaft 22 enables a drive coupling with a lancing drive that is not shown for a reciprocating lancing movement.

As only shown symbolically in FIG. 2b, a skin puncture 34 can be generated in a body part 36, for example a finger pad, by advancing the needle and in doing so the lancing component 16 can pierce through the protecting element 20. In this connection the front of the holding body 28 forms a stop on the skin surface. It is also conceivable that the holding body 28 is held back on an abutment on the instrument side. Body fluid emerges in the skin puncture 34 or in the wound channel which fills the collecting structure 18 during the lancing process if necessary by capillary action. In this case the collecting volume can be limited to microscopic amounts, for example a few nanoliters, in order to make the process as pain-free as possible.

FIG. 2c shows the microsampler 10 in the used state with a needle tip 16 exposed during the lancing operation and a retracted protecting element 20. In this state the liquid sample can be transferred directly from the collecting structure 18 onto a test element 12 without the user having to carry out further manipulations.

The embodiment shown in FIG. 3 in corresponding positions during the lancing operation differs from the example of FIG. 2 essentially only in that the holding body 28 only partially encloses the protecting foil 26 and the collecting structure 18 is limited to a small hole. In this case the holding body 28 is moulded onto the proximal end section of the protecting foil 26 by a ring-shaped injection moulding. The protecting foil 26 forms a two-layered pouch where a stiff foil layer ensures stability and on the other side a thin foil layer enables it to be easily pierced by the tip 16 without damage. In order to prevent an unintentional injury with the front side, a straight front edge is chosen.

FIG. 4 shows an embodiment example of a test device 10 having a guide chamber 38 as part of a magazine, for example in the form of a drum (not shown). The proximal shaft 22 of the lancing element can be coupled to a drive while the tip is stored in the protecting element 20. A test element 12 in the form of a dry chemical reagent layer is arranged on the guide chamber 38 which is assigned to the lancing element 14. The reagent layer reacts to glucose in an applied blood sample by a change in colour which can be detected photometrically.

In the storage state (FIG. 4a) the protecting element 20 is in a stop position in front of a puncture opening 40 of the guide chamber 38. During the lancing operation (FIG. 4b) the lancing element 14 is inserted into the skin through the protecting element 20 and the opening 40. Subsequently the retraction movement (FIG. 4c) takes place with a filled collecting structure 18. In this case the holding body 28 forms a guide member in the guide chamber 38 for controlling a transfer movement of the collecting structure 18 towards the test element 12. In this case the contour of the guide chamber is selected such that in the retracted state the collecting structure 18 is pressed onto the test element 12 so that liquid is transferred (FIG. 4d).

Figure 5D:
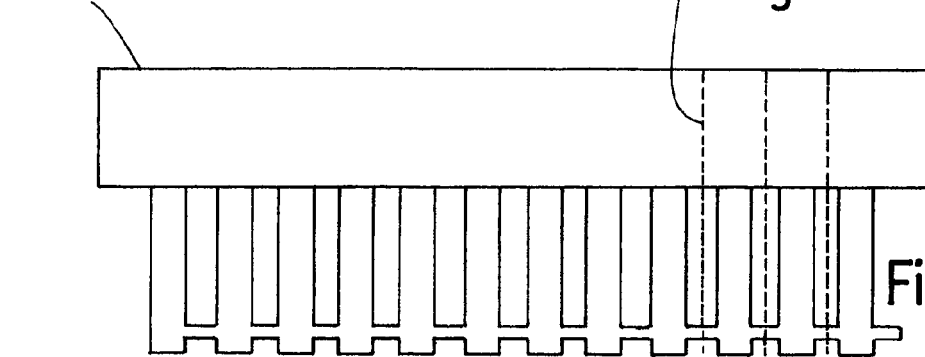

A cost-effective mass production is advantageous for the production of the microsamplers 10 as disposable parts. FIG. 5 illustrates various manufacturing stages of a roll-to-roll production. According to FIG. 5a the lancing elements 14 can be formed by etching from a metal tape as flat shaped parts, where the individual elements remain joined together by bridges 42. In a next step a thin foil tape 44 is placed on both sides over the needle tips 16 according to FIG. 5b so that the collecting structures 18 are also covered. Then the foil tapes 44 are joined together by double seams 46 in the spaces between the needle tips 16 according to FIG. 5c, for example by laser welding or heat sealing. Afterwards a cut is made between the individual seams so that each tip 16 rests in its own foil pouch 48. Subsequently this area on the tape is injection-moulded with an elastomer material 50 as shown in FIG. 5d. The individual lancing elements 14 can subsequently be produced by dividing the tape structure along the cutting lines 52 and optionally sterilized by irradiation.

What is claimed is:

1. A test device for blood sugar tests, comprising a lancing element which is provided with a lancing component for producing a skin puncture, and a protecting element shielding the lancing element at least in a region of the lancing component, wherein the lancing element has a collecting structure for collecting body fluid from the skin puncture and the protecting element has a protecting foil to cover the collecting structure, wherein the protecting element has an injection molded holding body directly molded onto the lancing element and configured for holding the protecting foil.

2. The test device according to claim 1, wherein the collecting structure is formed by a recess in the lancing component that can be filled with body fluid and is in a form of a groove that is open on one side or a cut-out that is open on both sides, and that the recess is covered by the protecting foil when the lancing element is in an unused state.

3. The test device according to claim 1, wherein the lancing element has a hydrophilic coating which is covered by the protecting foil at least in some areas.

4. The test device according to claim 1, wherein the protecting foil and the holding body are in a common movable arrangement on the lancing element or capable of being jointly removed from the lancing element, so that the lancing component and the collecting structure are exposed when the lancing element is in use.

5. The test device according to claim 1, wherein the lancing component can be inserted into the skin while piercing the holding body or the protecting foil.

6. The test device according to claim 1, wherein the protecting element forms a stop against the skin or against an abutment when the skin puncture is produced.

7. The test device according to claim 1, wherein the protecting foil forms a two-layered foil envelope or a single-layered foil cover.

8. The test device according to claim 1, wherein the protecting foil rests loosely on the lancing component or is releasably adhesively connected to the lancing component.

9. The test device according to claim 1, wherein the holding body forms a permanent composite with the protecting foil, wherein the holding body completely encloses the protecting foil or encloses the protecting foil at one end section.

10. The test device according to claim 1, wherein the holding body is made of an elastomer material.

11. The test device according to claim 1, wherein the holding body is molded to the lancing element adjacent an edge part reaching over the protecting foil in a germ-tight manner.

12. The test device according to claim 1, wherein the protecting element is designed to maintain a sterility of at least the lancing component in an unused state or to enable at least the lancing component to be hygienically disposed of in a used state.

13. The test device according to claim 1, wherein the collecting structure to which body fluid is applied can be brought into contact with an analytical test element that reacts to an analyte in the body fluid by means of a transfer movement so that body fluid is transferred from the collecting structure onto the test element.

14. The test device according to claim 1, wherein the holding body forms a guide member to control any movement of the lancing element.

15. A method for the production of a test device, comprising:
 providing a lancing element having a lancing component for producing a skin puncture and a collecting structure for collecting body fluid from the skin puncture,
 covering the lancing element with a protecting element comprising a protecting foil at least in the area of the collecting structure,
 providing an injection molded holding body directly molded onto the lancing element, configured for holding the protecting foil onto the lancing element, and
 incorporating the lancing element in the test device.

* * * * *